(12) United States Patent
Roccati et al.

(10) Patent No.: US 8,227,642 B2
(45) Date of Patent: Jul. 24, 2012

(54) PRODUCTION OF AMINES BY HYDROGENATION OF NITRILE COMPOUNDS

(76) Inventors: Philippe Roccati, Charnoz sur Ain (FR); Didier Letourneur, Lyons (FR); Philippe Denis, Decines (FR)

( * ) Notice: Subject to any disclaimer, the term of this patent is extended or adjusted under 35 U.S.C. 154(b) by 421 days.

(21) Appl. No.: 12/441,287

(22) PCT Filed: Sep. 13, 2007

(86) PCT No.: PCT/FR2007/001476
§ 371 (c)(1),
(2), (4) Date: Jan. 11, 2010

(87) PCT Pub. No.: WO2008/034964
PCT Pub. Date: Mar. 27, 2008

(65) Prior Publication Data
US 2010/0130789 A1    May 27, 2010

(30) Foreign Application Priority Data
Sep. 19, 2006  (FR) ................................ 06 08172

(51) Int. Cl.
*C07C 209/48*    (2006.01)

(52) U.S. Cl. .................. 564/492; 564/490; 564/491
(58) Field of Classification Search ............... None
See application file for complete search history.

(56) References Cited

U.S. PATENT DOCUMENTS

| 4,289,908 A | * | 9/1981 | Becker et al. ............... 564/490 |
| 5,840,989 A |   | 11/1998 | Cordier et al. |
| 5,869,653 A | * | 2/1999 | Johnson ..................... 540/531 |

FOREIGN PATENT DOCUMENTS

| FR | 2722784 | 1/1996 |
| WO | WO 95/17959 A1 | 7/1995 |
| WO | WO 98/43940 A1 | 10/1998 |
| WO | WO 00/37424 A1 | 6/2000 |

* cited by examiner

*Primary Examiner* — Brian J Davis
(74) *Attorney, Agent, or Firm* — SNR Denton US LLP

(57) ABSTRACT

A method for producing amines by the hydrogenation of nitrile compounds in the presence of a catalyst, notably a method for producing diamines by the continuous hydrogenation of dinitrile compounds in the presence of a Raney-metal catalyst, includes controlling the molar flow of nitrile compounds and the mass flow of catalyst in a hydrogenation piston reactor in order to minimize the occurrence of impurities and deterioration of the catalyst.

14 Claims, 2 Drawing Sheets

PRODUCTION OF AMINES BY HYDROGENATION OF NITRILE COMPOUNDS

CROSS-REFERENCE TO PRIORITY/PCT APPLICATIONS

This application claims priority under 35 U.S.C. §119 of FR 0608172, filed Sep. 19, 2006, and is a continuation/national phase of PCT/FR 2007/001476, filed Sep. 13, 2007 and designating the United States (published in the French language on Mar. 27, 2008, as WO 2008/034964 A1; the title and abstract were also published in English), each hereby expressly incorporated by reference in its entirety and each assigned to the assignee hereof.

The present invention relates to a process for the manufacture of amine compounds by hydrogenation of nitrile compounds in the presence of a catalyst.

It relates more particularly to a process for the manufacture of diamines by continuous hydrogenation of dinitrile compounds in the presence of a catalyst based on a Raney metal.

One of the processes for the manufacture of amine compounds used industrially is the catalytic hydrogenation of nitrile compounds.

Thus, hexamethylenediamine, which is an important chemical intermediate in the manufacture of numerous compounds or polymers, is predominantly produced by catalytic hydrogenation of adiponitrile.

Mention may be made, by way of example, of the processes for the hydrogenation of adiponitrile in the presence of a metal oxide as catalyst, such as iron oxide or cobalt oxide. These processes are generally carried out at high pressures and temperatures and often in the presence of ammonia.

Other hydrogenation processes widely used consist in employing, as catalyst, a system based on a Raney metal, more particularly Raney nickel or cobalt, in the presence of water and of a basic compound. In these processes, the reaction is carried out at relatively low pressures and temperatures and in the absence of ammonia. The latter hydrogenation processes with a catalyst based on a Raney metal can be carried out in certain reactor types. This is because, as the catalyst is pyrophoric, the reactors used have to make possible efficient control of the continuous introduction of the catalyst into the reaction medium. It is also necessary to control the amount of catalyst suspended in the reaction medium and to provide managed and controlled circulation of this suspension.

However, the activity of these catalysts can be strongly affected when they are used under certain conditions in processes for the hydrogenation of nitrile compounds.

A paper published in Chemical Engineering Science, Vol. 47, No. 9-11, 2289-94 (1992), indicates that nitrile compounds deactivate catalysts based on Raney nickel or cobalt. In order to avoid this deactivation, provision was made, in the paper published in Chemical Engineering Science, Vol. 35, 135-141 (1980), to use a reactor with a high rate of circulation of the reaction medium in order to obtain optimum mixing conditions and a turbulent flow in order to avoid the formation of regions exhibiting a high concentration of nitrile compounds. This is because a high concentration of nitrile compounds results in deactivation of the catalyst.

All these processes use, as solution for reducing the decline in the activity of the catalyst, systems which make it possible to have efficient mixing of the reaction medium and thus to have an identical concentration of reactants and an identical concentration of catalyst at any point in the reactor.

Such a mixing quality is difficult to obtain and requires complex devices, such as those described in Patent Application WO 00/37424, which relates to the use of static mixers for improving the quality of the mixing and the homogeneity of the concentrations at any point in the reactor.

In addition, these solutions cannot be applied when the hydrogenation reaction is carried out continuously in a reactor operating under plug-flow conditions, such as bubble columns operating with circulation of a suspended catalyst bed, reactors comprising a bubble column and a cyclone head for separating the gases, referred to hereinafter as reactors of RTC type.

One of the aims of the present invention is to provide a continuous process for the hydrogenation of nitrile compounds to give amine compounds in the presence of a catalyst based on Raney metal which makes it possible to limit the rate of decline in the activity of the catalyst while avoiding the formation of impurities difficult to separate from the amine formed.

To this end, the invention provides a continuous process for the manufacture of a compound comprising at least one amine functional group by hydrogenation of a compound comprising at least one nitrile functional group, characterized in that it consists in:

feeding a gas comprising hydrogen and a nitrile compound to a reactor of plug-flow type in which circulates a reaction medium comprising suspended particles of catalyst based on Raney metal, an inorganic base and water, withdrawing, at the outlet of the plug-flow reactor, a portion of the reaction medium comprising the amine compound after separation of the catalyst and recycling the other portion to the plug-flow reactor, recycling the separated catalyst to the plug-flow reactor, feeding a stream of fresh catalyst to the plug-flow reactor, and in that the flow rates for feeding nitrile compounds and/or catalyst to the plug-flow reactor are controlled in order to maintain a ratio P of the number of moles of nitrile compounds fed per unit of time to the flow rate by weight of catalyst in the plug-flow reactor of between 0.02 and 0.15 mol of nitrile compounds per kg of catalyst for a catalyst exhibiting an initial activity of between $15 \times 10^{-5}$ and $35 \times 10^{-5}$ mol of $H_2$/g of catalyst/s.

The flow rate by weight of catalyst can be obtained by the material balance of the device used or by analysis of the concentration of catalyst in the plug-flow reactor or in other parts of the plant, such as in the part providing the recycling of the reaction medium to the plug-flow reactor.

It can also be obtained by measuring the concentration of catalyst at various locations in the plant in which the catalyst circulates, such as, for example, in the recycling stream of the catalyst to the plug-flow reactor after separation from the reaction medium, and mathematical extrapolation while taking into account the hydrodynamics of the plant used for carrying out this reaction. This mathematical extrapolation or correlation between the measurement of the concentration of catalyst and the flow rate of catalyst in the plug-flow reactor is established for each plant by application of the hydrodynamic rules well known in the state of the art or by systematic measurements in order to establish a calibration curve or chart.

The activity of the catalyst is expressed by the molar amount of hydrogen consumed during the reduction of the adiponitrile to give hexamethylenediamine for a defined amount of Raney nickel catalyst per unit of time under conditions of temperature and pressure and a KOH/weight of catalyst ratio which are determined for the measurement method.

The initial activity of the catalyst is determined by carrying out the procedure described below:

50 ml of demineralized water deaerated with argon are poured into a 250 ml beaker.

Approximately 2 grams of slurry formed of catalyst to be analysed are withdrawn using a spatula.

The test sample is introduced into the beaker and approximately 100 ml of demineralized and deaerated water are added.

The medium is stirred in order to suspend the catalyst to be analysed.

The water is separated from the catalyst by placing a magnetic plate at the bottom of the beaker.

The demineralized and deaerated water is drained. 150 ml of demineralized water are poured into the beaker.

The beaker placed on the magnet: the aqueous washing liquor is drained and then 50 to 100 ml of deaerated water are added.

The catalyst is washed with demineralized and deaerated water. At the end of the washing operations, the pH of the water must be in the vicinity of 7.

A pycnometer is filled with the supernatant liquid of the catalyst.

The pycnometer is weighed in order to define the zero of the balance.

The pycnometer is removed from the balance.

A small amount of water is removed from the pycnometer with a pipette.

The catalyst is withdrawn from the beaker with the same pipette.

An amount of catalyst is introduced into the pycnometer and the pycnometer is readjusted with the supernatant liquid.

The pycnometer is weighed and the difference in weight (W) between the pycnometer filled with water plus the catalyst and the pycnometer filled with water is read.

The weight of catalyst $w_{catalyst}$ is equal to 1.15×W.

The amount of catalyst in the pycnometer is readjusted by repeating the above weighing operations until the desired amount is obtained:

The amount of catalyst to be withdrawn is advantageously equal to:

Approximately 0.4000 g precisely of spent, regenerated or fresh washed catalyst:

(0.3960 g ≤ $w_{catalyst}$ ≤ 0.4040 g)

The weight $w_{catalyst}$ of catalyst introduced into the pycnometer is recorded (accuracy: 0.0001 gram).

The clean and dry reactor and its support are placed on the tare balance. The balance is zeroed.

The contents of the pycnometer are decanted into a clean and dry reactor.

The pycnometer is rinsed with the necessary amount of demineralized water to collect all of the catalyst introduced into the pycnometer.

As much as possible of water is removed using the magnetic plate on the bottom of the reactor.

6.8N potassium hydroxide KOH is added to the catalyst using the suitable microsyringe, i.e. 47 µl.

The solution is made up with demineralized water in order to obtain a weight of solution in the reactor equal to 4.66 g.

37.8 g of pure HMD are added to the reactor.

The reactor is inserted into the pilot-scale device and heating is begun (set temperature at 80° C.)

The headspace of the reactor is purged 3 times with nitrogen.

The hydrogen supply is placed at a pressure of 50 bar.

The headspace of the reactor is purged with hydrogen by admission of hydrogen and discharge. The operation is repeated 3 times while maintaining or reestablishing the pressure in the hydrogen supply.

At the end of the three purges of the reactor with hydrogen, the reactor is pressurized to 20 bar of hydrogen.

Stirring is begun (set temperature of 80° C. and stirring rate of 2000 rev/min).

Approximately 6.00 grams precisely of adiponitrile are withdrawn with a glass syringe equipped with its extended needle.

The balance is zeroed with the charged syringe equipped with its needle.

The adiponitrile is introduced into a dropping funnel.

The empty syringe equipped with its needle is weighed.

The weight of adiponitrile $w_{ADN}$ introduced into the dropping funnel is recorded (it must be between 5.70 and 6.30 grams).

The reactor is placed under hydrogen pressure from the hydrogen supply and a pressure of 50 bar is reestablished in the supply. It is confirmed that the supply and reactor pressures remain constant.

Once the temperature and the stirring have been reached, the valve of the dropping funnel is opened, first slightly and then completely in a single operation, in order to introduce the AdN into the reactor.

The pressure inside the reactor should rise to 25 bar.

The feed of hydrogen to the reactor from the supply is kept open until the hydrogen pressure curve is stable.

Throughout the duration of the reaction, the hydrogen pressure in the supply is recorded as a function of the time.

When the hydrogen pressure in the reactor is stable, the hydrogen feed to the reactor is closed.

Heating of the reactor is halted and the reaction medium is cooled to a temperature of 45° C.

The reactor is slowly decompressed and stirring is halted.

The headspace of the reactor is purged three times with nitrogen.

The contents of the reactor are drained into a container with rinsing with demineralized water.

The activity of the catalyst is determined by the initial rate of the reaction, given by the following formula:

$$R_{initial} = \frac{4 \times w_{ADN}}{108 \times w_{catalyst} \times 60 \times \Delta t_{initial}}$$

$\Delta t_{initial}$ is the time in minutes which the hydrogenation would take if the catalyst were continually replaced during the reaction. It is determined by the abscissa of the point of intersection between the slope of the curve for recording the pressure at the start of the reaction and the slope at the end of the reaction, which is generally zero. This curve represents the variation in the hydrogen pressure in the supply as a function of the time.

The initial rate of hydrogenation is expressed in moles of $H_2$/g of cata/s.

By control of this ratio P for a catalyst exhibiting a catalytic activity in a specific range, the Applicant Company noticed, contrary to the teaching of the knowledge acquired with regard to this reaction, that the amine recovered comprises a very low proportion of impurities, in particular of diaminocyclohexane, and that the rate of decline in the activity of the catalyst is very low.

This is because it is known that, under certain conditions, adiponitrile can react to give, by hydrogenation, a cyclic diamine, diaminocyclohexane, which is difficult to separate from hexamethylene-diamine. Consequently, it is important to limit the formation of this cyclic diamine in order to obtain a hexamethylenediamine which can be purified with a minimum capital cost and a minimum energy consumption. It is known that this formation of impurities of diaminocyclohexane type can be limited if the ratio P of nitrile compounds to the weight of catalyst is high. However, under these conditions, it is also known that the rate of decline in the activity of the catalyst is high.

The Applicant Company also noticed that the hexamethylenediamine obtained by observing the operating characteristics described above exhibits a low concentration of impurities which are detected by UV analysis of the hexamethylenediamine, a purity characteristic generally expressed in the form of a UV index (Iuv). This index is obtained by measuring the UV absorbance at a wavelength of 275 nm of a 32.4% by weight aqueous HMD solution present in a cell with a length of 5 cm.

The invention provides conditions for carrying out the reaction which make it possible, on the one hand, to limit the formation of impurities of the diamino-cyclohexane (DCH) type and/or impurities which can be detected by UV analysis. These conditions correspond to the use of a high ratio P (molar flow rate of nitrile compound to flow rate by weight of catalyst in the plug-flow reactor) in combination with a catalyst exhibiting a specific catalytic activity. Under these conditions and although the ratio P is high, the rate of decline in the activity of the catalyst remains at a very low level, a result normally obtained for a low ratio P.

The process of the invention applies in particular and preferably to the hydrogenation of dinitrile compounds, such as adiponitrile, to give diamine compounds, such as hexamethylenediamine.

The process of the invention makes it possible, by the use of a ratio P, molar flow rate of nitrile compound to flow rate by weight of catalyst in the plug-flow reactor, within a given range for a specific field of activity of the catalyst, to simultaneously obtain very limited formation of impurities, such as, for example, cyclic diamines, and a reduced rate of decline in the activity of the catalyst.

According to one characteristic of the invention, the hydrogenation reaction is carried out in the presence of a solvent. Among the solvents which are suitable, the amine obtained by hydrogenation is the preferred solvent. Thus, in the case of the hydrogenation of adiponitrile, hexamethylenediamine is advantageously used as main component of the solvent. The concentration of amine in the solvent is advantageously between 50% and 99% by weight, preferably between 60 and 99% by weight, of the solvent.

The hydrogenation reaction is advantageously carried out in the presence of water as other component of the solvent. This water is generally present in an amount of less than or equal to 50%, advantageously of less than or equal to 20%, by weight, with respect to the total reaction medium, and more preferably still between 0.1% and 15% by weight.

In addition to or as substitute for the water, it is possible to use at least one other solvent of the alcohol type. Mention may be made, as suitable alcohols, for example, of methanol, ethanol, propanol, isopropanol, butanol, glycols, such as ethylene glycol, polyols or a mixture of these compounds.

The hydrogenation catalyst comprises a Raney metal, preferably, Raney nickel or Raney cobalt. Promoter elements can advantageously be used with the Raney metal. These promoter elements are chosen from the elements belonging to Groups IIB and IVB to VIIB of the Periodic Table of the Elements. Advantageously, the promoter elements are chosen from the group consisting of titanium, chromium, zirconium, vanadium, molybdenum, manganese, cobalt, nickel, zinc, iron and their combinations.

The hydrogenation reaction is carried out in the presence of a basic compound, preferably an inorganic base, such as LiOH, NaOH, KOH, RbOH, CsOH and their mixtures. NaOH and KOH are preferably used.

The amount of base added is determined in order to have at least 0.1 mol of base per kilogram of catalyst, preferably between 0.1 and 2 mol of base per kg of catalyst and more advantageously still between 0.3 and 1.5 mol of base per kg of catalyst.

The hydrogenation reaction is carried out at a temperature of less than or equal to 150° C., preferably of less than or equal to 120° C. and more preferably still of less than or equal to 100° C. The reaction temperature is generally between 50° C. and 100° C.

The hydrogen pressure in the reactor is between 0.10 and 10 MPa approximately.

According to a preferred embodiment of the invention, the hydrogenation reaction of the invention is carried out continuously in an apparatus or device described below with reference to the appended FIGS. 1 and 2, which represent block diagrams of an embodiment of an apparatus suitable for the implementation of the invention.

The apparatus suitable for the implementation of the process of the invention makes it possible to produce excellent gas/liquid contact, rapid and efficient separation of these two phases after contact, continuous separation of the hydrogenate and of the catalyst and the recycling of the latter, in a time compatible with the least possible deactivation of the said catalyst.

The said apparatus comprises three main sections: a reaction section operating according to the principle of the bubble column with circulation of a suspended catalyst bed,
a gas/liquid separation section and a catalyst/liquid separation section with recycling of the said catalyst and withdrawing of the liquid (hydrogenate).

The reaction section generally comprises one or more U-shaped pipes, the branches of which are vertical or slightly inclined with respect to the vertical, one of the branches of each U providing the ascent of the gas/liquid/solid catalyst dispersion and the other the return of the at least partially degassed liquid. It also comprises four inlets at the base of the ascending branch: the hydrogen inlet, the dinitrile inlet, the fresh catalyst, with or without cocatalyst, inlet and the recycled catalyst inlet.

The gas/liquid separation section is composed of a vertical cylinder comprising one or more tangential inlets (coming from the ascending branch of the reactor), one or more tangential outlets (towards the descending branch of the reactor), a gas outlet and an outlet for the reaction mixture towards the liquid/solid separation. The inlet for the gas/liquid/solid catalyst dispersion is inserted at a point situated above the point of departure of the degassed liquid. This part forms a cyclone head.

The liquid/solid separation section is composed of a decanter which makes it possible to separate the hydrogenate from the catalyst and to recycle the said catalyst. The hydrogenate is withdrawn continuously, whereas the catalyst suspension separated in the decanter is brought back to the reaction section upstream of the point of introduction of the hydrogen. A bleed is carried out when it is judged necessary to replace a portion of the catalyst by fresh catalyst.

The term "fresh catalyst" should be understood as meaning, in the present text, either a "virgin" catalyst, that is to say having never been used in a hydrogenation reaction, or a mixture of virgin catalyst and of regenerated catalyst or also solely regenerated catalyst. The fresh catalyst can be introduced into the reactor after mixing the virgin and regenerated catalyst or in the form of two separate streams of virgin catalyst and regenerated catalyst.

Figure 1:
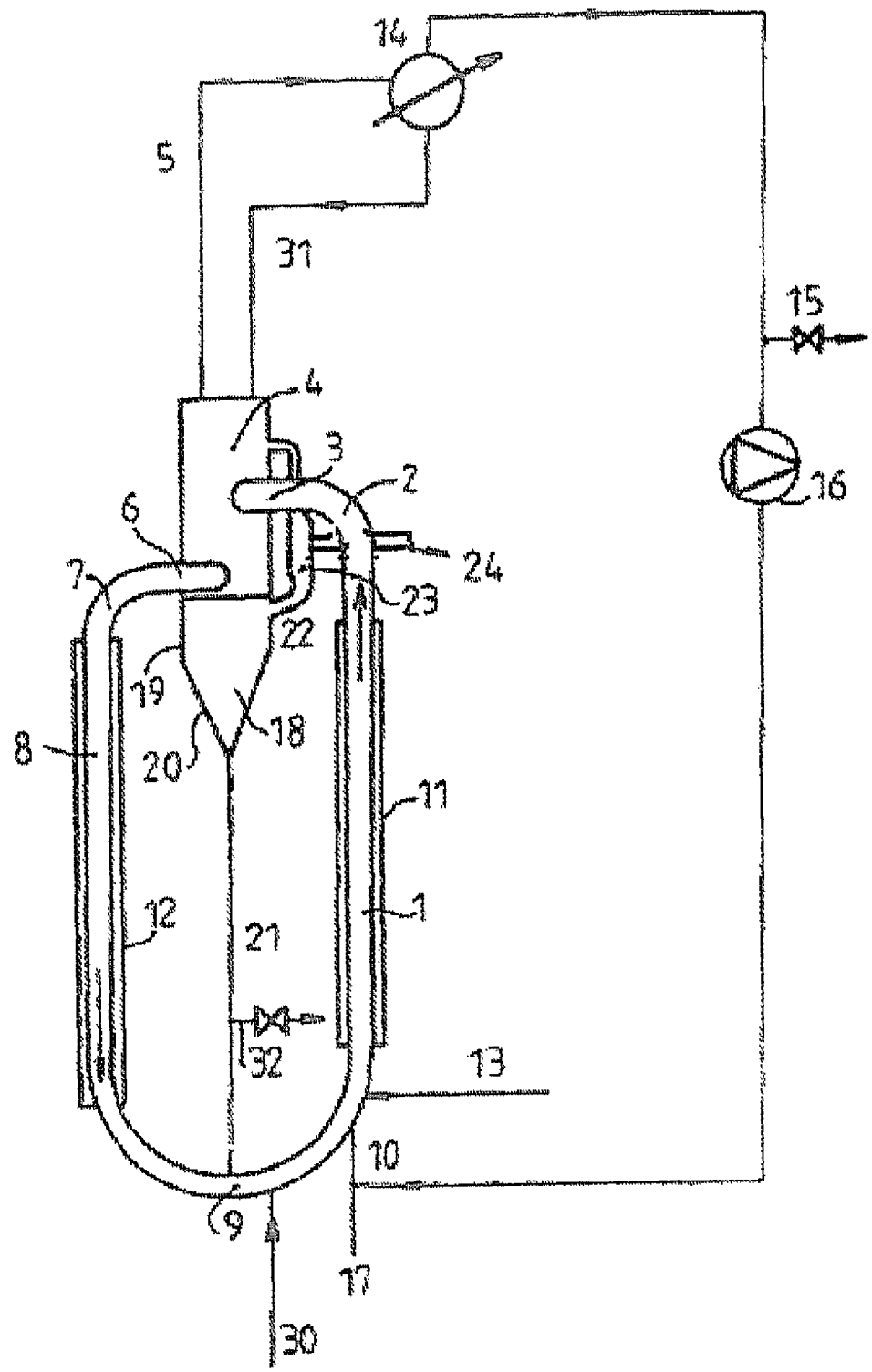
FIG. 1 is a block diagram of an embodiment of an apparatus suitable for the implementation of the invention.

The apparatus suitable for the process of the invention can be illustrated by way of example by FIG. 1. It comprises a vertical cylindrical pipe (1) connected by an elbowed pipe (2) to a horizontal pipe (3) emerging tangentially in a gas/liquid separator (4) composed of a vertical cylinder with a diameter greater than that of the pipe (1).

The separator (4) comprises a line (5) for discharge of gas or of vapours. A horizontal pipe (6) originating tangentially to the separator and at a point situated below the inlet point of the pipe (3) is connected via an elbowed pipe (7) to a second vertical pipe (8) communicating with the pipe (1) via an elbow (9). The combination of the pipes (1) and (8) and of the elbow (9) forms a U. The pipe (1) comprises, at its base, a line (10) for introducing hydrogen and a line (13) for introducing the dinitrile. The pipes (1) and (8) can comprise, as represented in FIG. 1, a jacket (11) and (12) allowing the circulation of a cooling or heating fluid. The elbow (9) comprises an inlet (30) for fresh catalyst and an inlet (21) for recycled catalyst.

The pipes (1) and (8) can be vertical or slightly oblique (in the latter case, preferably so that their axes converge downwards).

The radii of curvature of the elbows (2, 7, 9) are calculated according to the usual rules of chemical engineering so that the pressure drop in the body circulating throughout the circuit is as low as possible. Their angle of curvature can vary from 45° to 135° and preferably from 60° to 120°.

In FIG. 1, the hydrogen is introduced via a line (10). This line can be equipped with any standard dispersing device but a simple pipe flush with the wall, positioned in the axis of the pipe (1), is sufficient. This line (10) is connected to a hydrogen source and the hydrogen can be introduced at atmospheric pressure or at a higher pressure.

The line (5) for discharge of the gases can be connected to any device for the treatment of the gases separated from the hydrogenate. FIG. 1 illustrates a device according to which the gases resulting from (5) pass into a condenser (14) in which the vapours entrained in the separator (4) are separated from the hydrogen. The condensate obtained is recycled to the apparatus via a line (31). The excess hydrogen subsequently passes into a compressor (16) via a pipeline comprising a bleed system (15) and then it is recycled in (10) after introduction, in (17), of an amount of hydrogen intended to compensate for the hydrogen consumed during the hydrogenation and that which has been bled off.

It is necessary to withdraw the hydrogenate formed degassed and freed from the catalyst. In order to be able to withdraw a clear hydrogenate, that is to say comprising virtually no catalyst, a decanter (18) is placed directly under the separator (4). The liquid/catalyst suspension, the gas phase of which had been separated in the separator (4), enters the decanter (18).

The decanter (18) is composed of a cylinder (19) terminated by a cone (20).

A pipeline (21) serves to continuously return the concentrated catalyst slurry to the elbow (9). The hydrogenate, freed from the catalyst, exits via a pipeline (22) connected to a trap (23) equipped with an overflow (24) which makes it possible to continuously withdraw the clear hydrogenate, the level in the whole of the apparatus being kept constant by the continuous introduction of an equivalent volume of dinitrile, solvent and catalyst mixture. The catalyst decanted in the cone (20) is recycled to the pipe (9) via the line (21). The line (21) comprises a line (32) for bleeding off the spent catalyst, which can optionally be regenerated.

Figure 2:
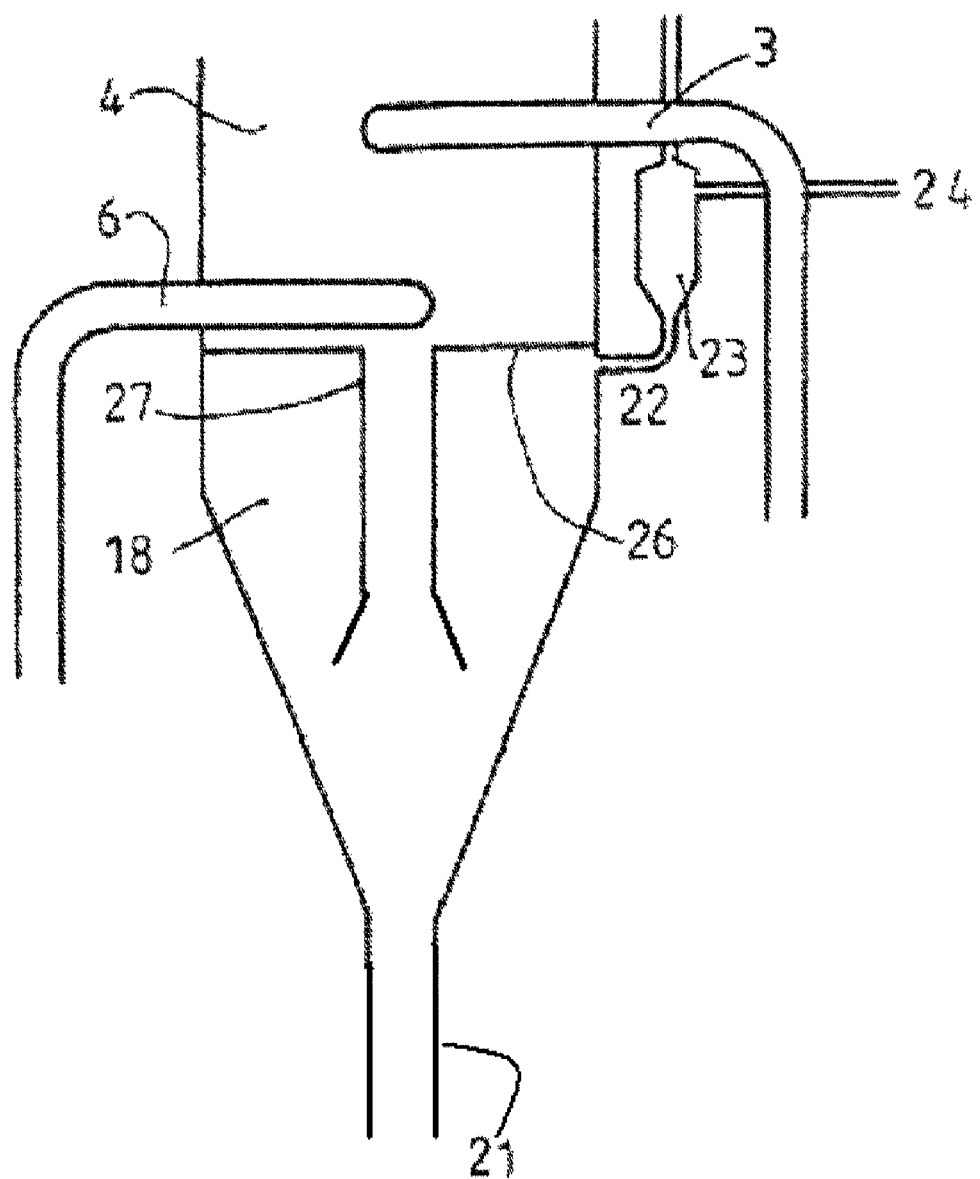
FIG. 2 illustrates a specific form of decantation within the scope of the invention.

FIG. 2 illustrates in more detail a specific form of decantation coming within the scope of the invention. To prevent, on the one hand, the excessively rapid movements of the mass of catalyst and of hydrogenate from being propagated in the decanter (18) and, on the other hand, the hydrogen from entering the latter, separation between the two regions (gas/liquid separation section and liquid/solid separation section) is necessary. However, it must not in any way be the cause of deposition of catalyst. Such a result is obtained by virtue of the installation of a partition (26) between the separator (4) and the decanter (18), the circulation between the gas/liquid separator and the decanter being provided by a pipeline (27) with a diameter calculated in order to significantly reduce the velocity of the liquid (for example to a value of less than 0.5 metre/second).

This pipeline (27) is extended inside the decanter by a pipe with a diameter greater than or equal to that of the pipeline (27).

The use of the device or installation described above for carrying out the process for the hydrogenation of adiponitrile to give hexamethylenediamine makes it possible to obtain good dispersion of the hydrogen in the liquid reaction mixture. This dispersion is stable and homogeneous throughout the U-shaped pipe or pipes. This apparatus makes it possible, as was said above, to continuously separate, and without significant deactivation of the catalyst, the hydrogenate to be withdrawn from the said catalyst to be recycled.

In such an apparatus, the abovementioned ratio P of the molar flow rate of nitrile compound to the flow rate by weight of catalyst is that existing in the reaction region or plug-flow reactor corresponding to the pipe (1). However, in order to determine the flow rate by weight of catalyst, the existing concentration of recycled catalyst in the pipe (21) for recycling the catalyst or the concentration of catalyst in the pipe (8) for returning the reaction medium will advantageously be determined.

Other details or advantages of the invention will become more clearly apparent in the light of the examples given below purely by way of illustration.

EXAMPLE 1

Adiponitrile is continuously hydrogenated to hexa-methylenediamine at a temperature of 82° C. and a pressure of 23 bar in an installation represented in FIG. 1. The reaction medium comprises adiponitrile fed via the pipe (13), hydrogen fed via the pipe (17), potassium hydroxide, hexamethylenediamine, water and a catalyst comprising Raney nickel.

The catalyst exhibits an activity of $26 \times 10^{-5}$ mol of $H_2$/g of catalyst/second, measured according to the test described above. The concentration of the catalyst and the feed flow rate of the adiponitrile are adjusted in order to obtain a factor P in the hydrogenation reactor (1) of between 0.041 and 0.054 mol of AdN/kg of catalyst.

The hexamethylenediamine recovered in (24) exhibits the following purity characteristics (measured according to the methods described above or conventional techniques):
concentration of diaminocyclohexane (DCH): 1900 ppm
Iuv: 1.5

EXAMPLE 2

Example 1 was repeated with a catalyst exhibiting an activity of $42\times10^{-5}$ mol of $H_2$/g of catalyst/second, the concentration of the catalyst and the AdN flow rate in the reactor (1) being fixed in order to obtain a factor P in the reactor of between 0.042 and 0.055 mol of AdN/kg of catalyst.

The hexamethylenediamine recovered in (24) exhibits the following purity characteristics:
concentration of diaminocyclohexane (DCH): 3500 ppm
Iuv: 5

These tests clearly show the influence of the activity of the catalyst for a factor P within a certain range on the quality of the hexamethylenediamine produced at the reactor outlet.

The invention claimed is:

1. A continuous process for the synthesis of compounds containing at least one amine functional group by hydrogenation of compounds containing at least one nitrile functional group, comprising:
feeding a gas which comprises hydrogen and a nitrile compound to a plug-flow reactor in which circulates a reaction medium comprising suspended particles of catalyst based on Raney metal, an inorganic base and water;
withdrawing, at the outlet of the plug-flow reactor, a portion of the reaction medium comprising the amine compound after separation of the catalyst and recycling the other portion to the plug-flow reactor;
recycling the separated catalyst to the plug-flow reactor;
feeding a stream of fresh catalyst to the plug-flow reactor; and further wherein the flow rates for feeding nitrile compounds and/or catalyst to the plug-flow reactor are controlled as to maintain a ratio P of the number of moles of nitrile compounds fed per unit of time to the flow rate by weight of catalyst in the plug-flow reactor of from 0.02 to 0.15 mol of nitrile compounds per kg of catalyst for a catalyst exhibiting an initial activity of from $15\times10^{-5}$ to $35\times10^{-5}$ mol of $H_2$/g of catalyst.

2. The continuous process as defined by claim 1, wherein the reaction medium comprises a solvent.

3. The continuous process as defined by claim 2, wherein the solvent comprises the amine produced by the hydrogenation reaction.

4. The continuous process as defined by claim 1, wherein the nitrile compound is adiponitrile and the amine synthesized is hexamethylenediamine.

5. The continuous process as defined by claim 1, whereat the outlet of the plug-flow reactor is a region for decantation of the catalyst particles, the supernatant phase being recycled to the plug-flow reactor via a first external loop comprising a withdrawal of the medium comprising the amine, the decanted phase being recycled to the plug-flow reactor via a second external loop.

6. The continuous process as defined by claim 5, comprising withdrawing spent catalyst from the second external loop and feeding fresh catalyst at the inlet of the plug-flow reactor or to the second external loop.

7. The continuous process as defined by claim 6, wherein the fresh catalyst comprises virgin catalyst, regenerated catalyst or mixture thereof.

8. The continuous process as defined by claim 5, comprising a determination of the concentration of catalyst in the second external loop in order to calculate the total weight of catalyst in the plug-flow reactor.

9. The continuous process as defined by claim 1, wherein the catalyst is based on Raney nickel or Raney cobalt.

10. The continuous process as defined by claim 9, wherein the catalyst comprises a promoter selected from the elements of Groups IIB and IVB to VIIB of the Periodic Table of the Elements and combinations thereof.

11. The continuous process as defined by claim 1, wherein the inorganic base is selected from the group consisting of LiOH, NaOH, KOH, RbOH, CsOH and mixture thereof.

12. The continuous process as defined by claim 11, wherein the inorganic base is selected from the group consisting of KOH and NaOH and mixture thereof.

13. The continuous process as defined by claim 11, wherein the amount of base in the reaction medium ranges from 0.1 mol of base per kg of catalyst to 2 mol of base per kg of catalyst.

14. The continuous process as defined by claim 1, wherein the reaction temperature ranges from 50° C. to 150° C. and the hydrogen pressure ranges from 0.1 MPa to 10 MPa.

* * * * *

UNITED STATES PATENT AND TRADEMARK OFFICE
CERTIFICATE OF CORRECTION

| | | |
|---|---|---|
| PATENT NO. | : 8,227,642 B2 | Page 1 of 1 |
| APPLICATION NO. | : 12/441287 | |
| DATED | : July 24, 2012 | |
| INVENTOR(S) | : Philippe Roccati et al. | |

It is certified that error appears in the above-identified patent and that said Letters Patent is hereby corrected as shown below:

Title Page, Section 73 (Assignee): please add --Rhodia Operations, Aubervilliers (FR)--

Signed and Sealed this
Twenty-fifth Day of December, 2012

David J. Kappos
*Director of the United States Patent and Trademark Office*